United States Patent [19]

Kuzma

[11] Patent Number: 5,562,716
[45] Date of Patent: Oct. 8, 1996

[54] PACKAGE AND METHOD OF CONSTRUCTION

[75] Inventor: Janusz Kuzma, Lane Cove, Australia

[73] Assignee: Cochlear Limited, Lane Cove, Australia

[21] Appl. No.: 407,008

[22] PCT Filed: Oct. 20, 1993

[86] PCT No.: PCT/AU93/00535

§ 371 Date: Mar. 29, 1995

§ 102(e) Date: Mar. 29, 1995

[87] PCT Pub. No.: WO94/08539

PCT Pub. Date: Apr. 28, 1994

[30] Foreign Application Priority Data

Oct. 20, 1992 [AU] Australia .................... PL5382

[51] Int. Cl.$^6$ ...................................... A61N 1/375
[52] U.S. Cl. ............... 607/36; 228/262.21; 228/175; 65/59.1
[58] Field of Search ............... 228/262.21, 175, 228/124.6, 193; 65/59.1, 59.3, 59.4; 607/36

[56] References Cited

U.S. PATENT DOCUMENTS

| | | | |
|---|---|---|---|
| 4,050,956 | 9/1977 | de Bruin | 148/6 |
| 4,517,738 | 5/1985 | Fukuoka et al. | 228/175 |
| 4,693,409 | 9/1987 | Mizunoya et al. | 228/262.21 |
| 4,991,582 | 2/1991 | Byers | 128/419 P |
| 5,046,242 | 9/1991 | Kuzma | 29/878 |

FOREIGN PATENT DOCUMENTS

| | | |
|---|---|---|
| 1426873 | 3/1976 | United Kingdom . |
| 2061155 | 5/1981 | United Kingdom . |

Primary Examiner—William E. Kamm
Assistant Examiner—Kennedy J. Schaetzle
Attorney, Agent, or Firm—Gottlieb, Rackman & Reisman, P.C.

[57] ABSTRACT

A package for use in implanted devices, particularly where power and/or data are supplied by an inductive link, is disclosed. A ceramic envelope is bonded to a platinum or similar flange, so that the package may be sealed by simply welding the flange to a metal closure. No braze is required in the bonding of the flange to the envelope.

6 Claims, 3 Drawing Sheets

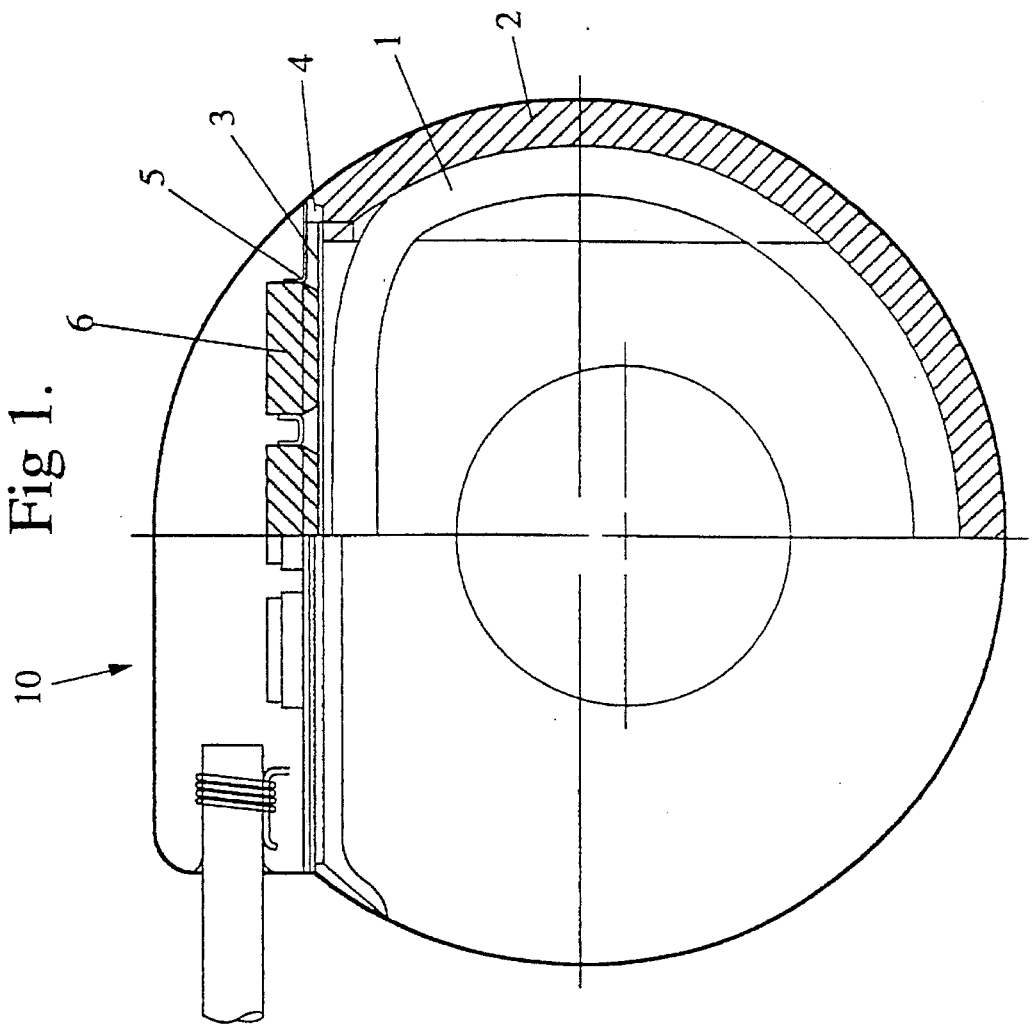
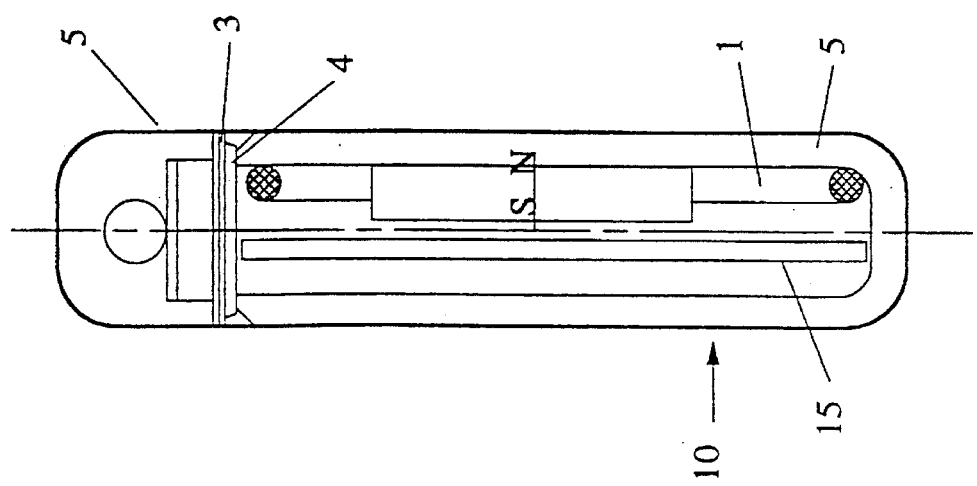

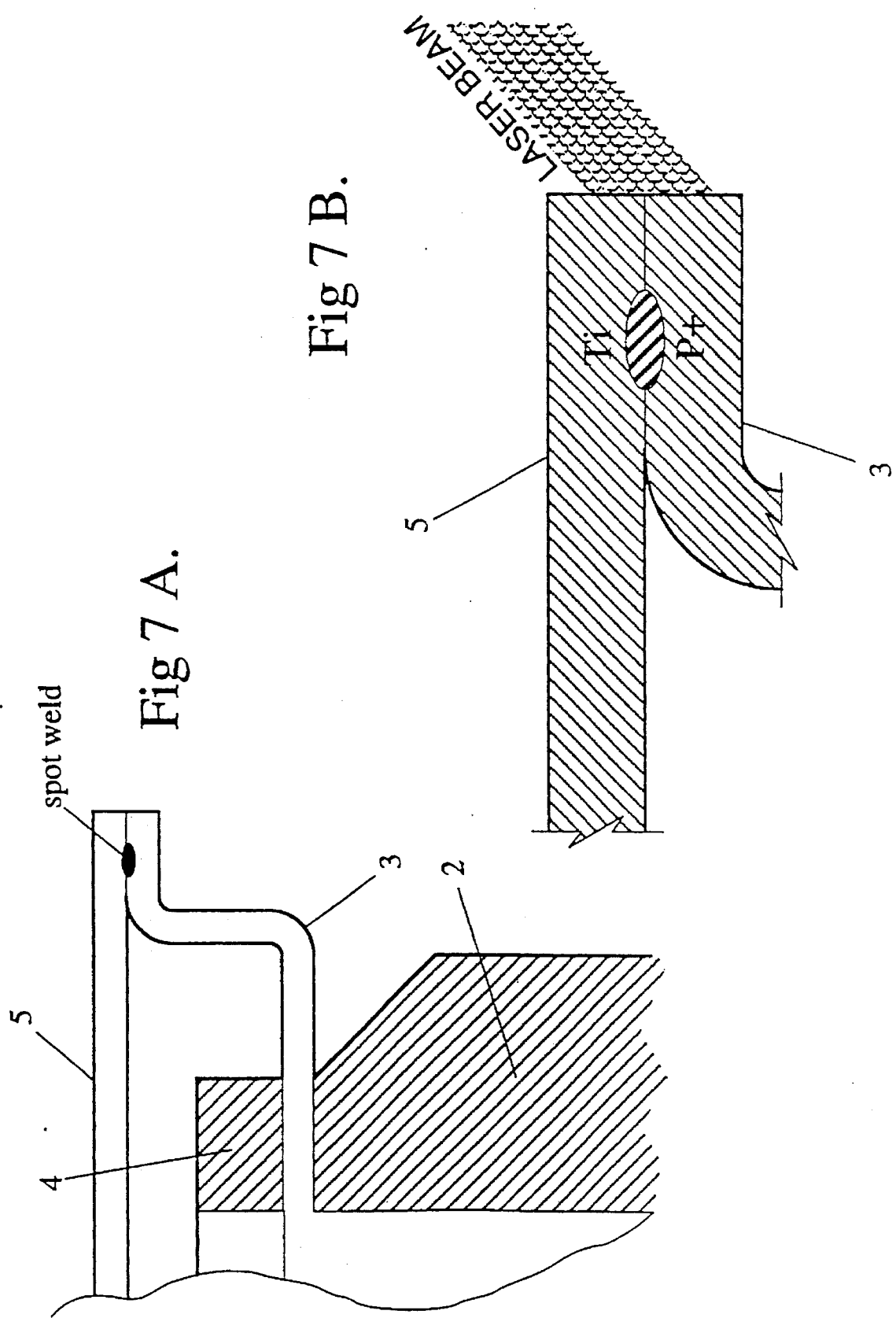

PACKAGE AND METHOD OF CONSTRUCTION

FIELD OF INVENTION

This invention relates to a construction and method for sealing of a ceramic-metal package, particularly but not exclusively a package for an implantable device.

BACKGROUND OF INVENTION

For implanted devices which acquire power from an external source, a key aspect for satisfactory performance is the efficiency of power transmission to the implanted device. In devices such as cochlear implants, the technique of using an inductive link to transfer power and/or data to the implanted device has been used. Conventional metal packages reduce the efficiency of inductive transfer. One way to address this problem is by utilising a ceramic package containing the receiving coil, instead of the conventional metal package. This arrangement provides reduced attenuation of the RF Field. However, such a package must be effectively sealed, without damaging the components within the package.

One prior art technique is disclosed in U.S. Pat. No. 4,991,582 to Byers et al. Here, the open end of the ceramic package is closed using a metal band bonded to the open end of the package using a metallic braze, and the band is ultimately sealed to a header by spot welding. A similar arrangement is disclosed in U.S. Pat. No. 4,785,827 to Fischer.

in these arrangements, the biocompatability of the resulting package may be compromised by the materials used, particularly the braze. There is also a the risk of degradation or corrosion along, or as a result of, the braze.

SUMMARY OF INVENTION it is an object of the present invention to provide a ceramic package suitable for use with an implanted device, which avoids the need for brazes in manufacture.

According to one aspect the present invention comprises a hermetically sealed package for an implanted device comprising:

a ceramic envelope;

a metal flange bonded thereto without braze, and a metal or metal composite closure attached to said flange.

Preferably, the package further includes a further ceramic element bonded to the other side of said flange so as to provide a surface for compression during the bonding procedure.

Preferably a further element is provided adjacent to said flange so as to distribute stresses over the flange/envelope bond. Preferably the further element is a washer.

According to another aspect the present invention comprises a method of forming a weld sealable implantable package, comprising solid state bonding a metal flange to a ceramic envelope by compressing them together at a temperature and pressure and for a duration sufficient to effect bonding.

Preferably said method further comprises bonding a further ceramic element to the other side of said flange.

BRIEF DESCRIPTION OF DRAWINGS

One embodiment of the invention will now be described with reference to the accompanying drawings, in which:

FIG. 1 illustrates a package formed according to the invention, partly in section;

FIG. 2 illustrates the package of FIG. 1 in section about a perpendicular axis;

FIGS. 7A and 7B illustrate the preferred bonding of the hermetic seal according to one aspect of the invention.

DISCLOSURE OF INVENTION

The present invention uses a solid non-liquid bonding technique to join the ceramic envelope to a platinum flange, and then the flange is bonded to a feedthrough assembly at a later point. The advantage of this arrangement is that no brazing is required during manufacture. Additionally, the resulting construction is structurally sound, and can be readily sealed by welding.

Figure 3:
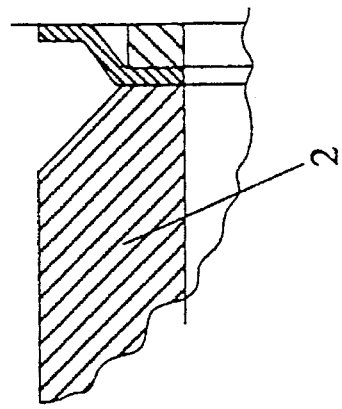
FIG. 3 illustrates in more detail the bonded flange joint according to this embodiment.

FIGS. 1 and 2 illustrate the assembled package 10 according to the preferred embodiment of the present invention. Ceramic envelope 2 encloses RF receiving coil 1, feedthrough assembly 5, and the other operative components of a cochlear implant receiver-stimulator unit. The precise operation and configuration of the implanted device are irrelevant to the present invention. The envelope 2 may be made from any suitable ceramic, preferably a high alumina ceramic. The envelope 2 is bonded to platinum flange 3, and flange 3 to ceramic washer 4, as can be seen more clearly from FIG. 3.

This "sandwich" construction is preferably formed according to the solid state bonding techniques disclosed in U.S. Pat. No. 4,050,956 to deBruin et al. Reference to that document should be made if further details are required, or in particular if the reader wishes to vary from the specific technique disclosed herein. The present invention is not limited to this particular technique of bonding, although this technique is presently preferred.

More particularly, the flange 3, envelope 2 and washer 4 are preferably compressed at a temperature of about 1200° C. for about 12 hours, under a force of about 10N. The surfaces to be bonded are preferably clean, and well fitting. This produces a flat, smooth surface and a construction which is hermetically bonded, without the use of any braze, and without melting any components. The bond thereby produced is very strong and resistant to thermal and mechanical shocks. This results both from the nature of the procedure, and from the materials selected.

It will be appreciated that other ceramics and related materials, such as glasses, and other metals, such as platinum alloys or other biocompatible metals, may be substituted in the construction, subject to physical properties and biocompatability.

It is noted that it has been experimentally observed that a temperature of about 1200° C. is preferred, contrary to theory which would suggest that about 0.9 of the melting point of Pt, or around 1600° C. should be optimal.

Of course, it will be apparent that the above parameters may be varied considerably while still resulting in a suitable bond.

It will be appreciated that all materials used are well established as biocompatible, and hence this significant problem with prior art techniques is obviated. Moreover, the package exhibits greater mechanical strength and thermal stability than the prior art technique. It is noted that the inventive technique also allows for a substantially smaller package to be produced, as a result of the smaller dimensions required for a join according to the present invention. This is a significant advantage for implanted devices.

The washer 4 is provided primarily so as to enable the join to be formed it will be appreciated that if another piece of (e.g) ceramic were used to engage the Pt surface during the bonding process, it would itself be bonded to the Pt. Further, the washer operates to distribute stresses incurred during welding and other procedures over the whole of the bond, thus improving the mechanical properties of the flange assembly.

It will be understood that once the platinum flange is attached, the envelope may be readily sealed by known welding techniques to metals once the operative components have been inserted.

Figure 6:
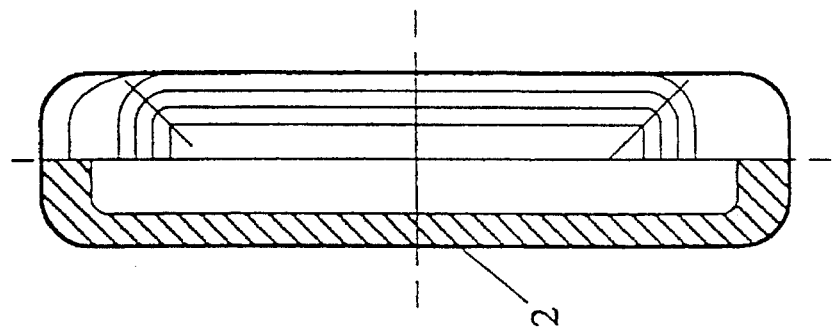
FIG. 6 is a view into the unsealed package.
Figure 4:
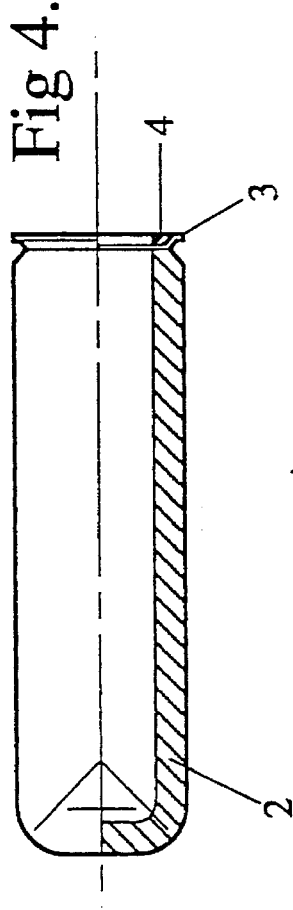
FIGS. 4 and 5 are further views illustrating this joint.
Figure 5:
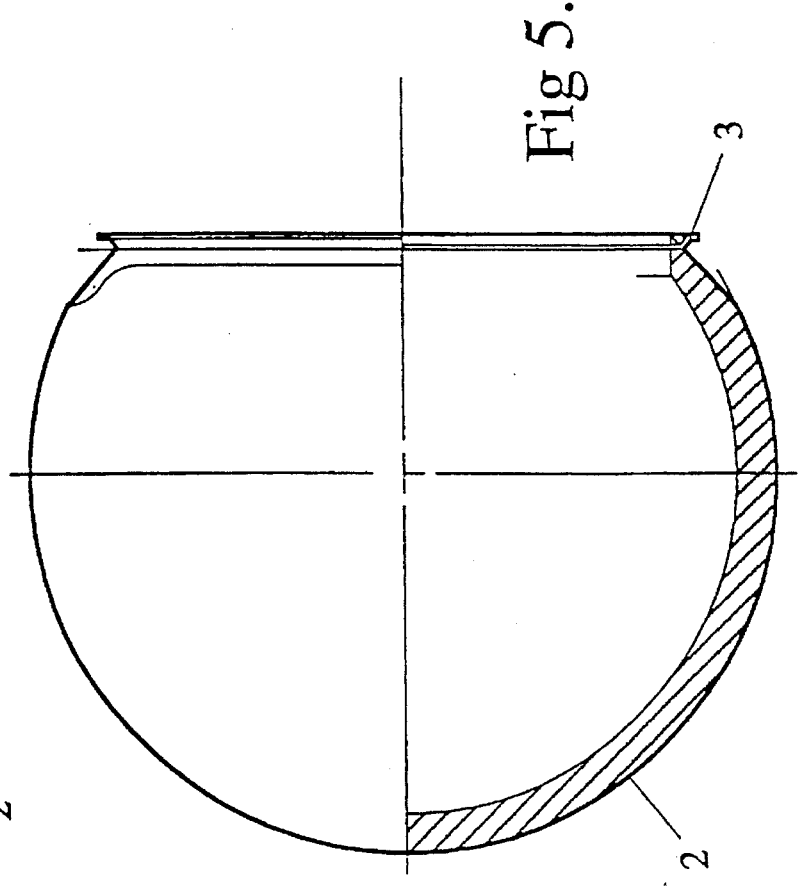

FIGS. 4, 5 and 6 show the ceramic envelope with the washer and flange attached. It will be apparent that flange 3 has a very small cross-sectioned area, which may be kept to below about 1 mm$^2$, so as to minimise electrical losses in use.

It will be appreciated that the flange may be formed from any biocompatible metal suitable for use in this bonding process, although platinum is preferred. Similarly, the ceramic washer is not essential to the invention.

The flange is illustratively joined to feedthrough assembly 5, which may be formed from any suitable material. In the instant example, it may be formed from Titanium with feedthroughs 6 formed from ceramic with platinum connections. Preferably, the feedthrough assemblies are formed from Pt pins sintered in situ with the ceramic powder. It will be understood that this Pt-ceramic join need only be hermetic and is not structural. The feedthroughs 6 may be joined to the titanium flange by any suitable means, preferably using a titanium alloy braze as is known in the art.

After assembly, the feedthrough assembly 5 is joined to the flange 3 by spot welding, followed by laser welding of the joined edges. This procedure must, of course, be carried out so as to minimise unnecessary heating of the package so that the electronics are not damaged.

One difficulty with welding such a combination of materials by laser is that the platinum component is highly reflective. Thus, much of the incident laser energy may be reflected and not effectively transferred so as to melt the platinum.

One aspect of the present invention provides means to avoid this by first melting the titanium, and so indirectly transferring the laser energy to the platinum by the melted titanium. The liquid titanium is much more efficient at absorbing the incident laser energy. This allows for more controlled welding at the Ti-Pt join.

We claim:

1. A method of forming an implantable package for a device, comprising the steps of:
   (1) solid state bonding to each other, without braze, a metal flange having two faces, a ceramic washer engaging one face of said flange, and a ceramic envelope adapted to receive said device and engaging the other face of said flange, with a peripheral region of said flange at each face thereof left exposed to enable a metal closure to be welded to said flange, by compressing said ceramic washer, said metal flange and said ceramic envelope together as a sandwich construction at a temperature and pressure and for a duration sufficient to effect bonding;
   (2) inserting said device into said ceramic envelope; and
   (3) welding a metal closure to said flange at said exposed peripheral region thereof so as to seal said package.

2. A method according to claim 1, wherein said ceramic washer, said metal flange and said ceramic envelope are compressed under a pressure of about 10N and at a temperature of at least about 1200° C. for at least about 12 hours.

3. An implantable package formed according to the method of claim 1.

4. A method of forming a weld sealable implantable package, comprising solid state bonding a sandwich construction comprising a metal flange, a ceramic envelope and a ceramic washer by compressing them together at a temperature and pressure and for a duration sufficient to effect bonding, the arrangement being such that an edge region of said flange is left exposed around said ceramic washer so as to operatively enable welding of a metal closure for said package to said flange.

5. A method according to claim 4, wherein said ceramic washer, said metal flange and said ceramic envelope are compressed under a pressure of about 10N and at a temperature of at least about 1200° C. for at least about 12 hours.

6. A weld sealable implantable package formed according to the method of claim 4.

* * * * *